United States Patent
Hu

(10) Patent No.: US 10,930,399 B2
(45) Date of Patent: Feb. 23, 2021

(54) SYSTEM AND METHOD TO PRODUCE AND VALIDATE WEIGHTED RELATIONS BETWEEN DRUG AND ADVERSE DRUG REACTIONS

(71) Applicant: FUJITSU LIMITED, Kawasaki (JP)

(72) Inventor: Bo Hu, Winchester (GB)

(73) Assignee: FUJITSU LIMITED, Kawasaki (JP)

(*) Notice: Subject to any disclaimer, the term of this patent is extended or adjusted under 35 U.S.C. 154(b) by 881 days.

(21) Appl. No.: 15/443,427

(22) Filed: Feb. 27, 2017

(65) Prior Publication Data

US 2017/0316175 A1 Nov. 2, 2017

(30) Foreign Application Priority Data

Apr. 29, 2016 (DE) .......................... 102016207473.3
Apr. 29, 2016 (GB) ..................................... 1607496

(51) Int. Cl.
*G16H 50/70* (2018.01)
*G06F 16/951* (2019.01)
(Continued)

(52) U.S. Cl.
CPC ....... *G16H 50/70* (2018.01); *G06F 16/24578* (2019.01); *G06F 16/951* (2019.01);
(Continued)

(58) Field of Classification Search
CPC ........ G16C 20/30; G16H 50/70; G16H 50/20; G16H 70/40; G16H 10/20; G06F 16/24578; G06F 16/951; G06N 5/022; G06N 7/025
See application file for complete search history.

(56) References Cited

U.S. PATENT DOCUMENTS

2013/0013332 A1 1/2013 Frieder et al.
2013/0066903 A1* 3/2013 Tymoshenko .......... G06F 19/00
707/769
(Continued)

FOREIGN PATENT DOCUMENTS

WO WO 2009/105114 A1 8/2009
WO WO 2015/023188 A1 2/2015
(Continued)

OTHER PUBLICATIONS

Liu, "Identifying Adverse Drug Events from Patient Social Media: A Case Study for Diabetes," in 30.3 IEEE Intelligent Sys. 44-51 (2015). (Year: 2015).*
(Continued)

*Primary Examiner* — Kamran Afshar
*Assistant Examiner* — Ryan C Vaughn
(74) *Attorney, Agent, or Firm* — Staas & Halsey LLP

(57) ABSTRACT

A processor is to monitor social media for links between a drug and an adverse drug reaction (ADR), and to extract a relation between the drug and the ADR using named entity recognition to provide a weighted social media relation between the drug and the ADR. The weighted social media relation is based on a confidence of a link between the drug and the ADR. A domain knowledge of ontologies of drug names and/or ADRs is used to refine the weighted social media relation and to quantify the weighted social media relation by using drugs and ADR links extracted from research publications and/or from clinical trial reports, to provide a research weight for the weighted social media relation; and/or by using a search engine to search the Internet for the drug and the ADR, where a number of hits quantifies an internet weight for the weighted social media relation.

10 Claims, 13 Drawing Sheets

(51) Int. Cl.

| | | |
|---|---|---|
| *G06F 16/2457* | (2019.01) | |
| *G16C 20/30* | (2019.01) | |
| *G16H 10/20* | (2018.01) | |
| *G16H 50/20* | (2018.01) | |
| *G16H 70/40* | (2018.01) | |
| *G06N 5/02* | (2006.01) | |
| *G06N 7/00* | (2006.01) | |

(52) U.S. Cl.
CPC ............ *G06N 5/022* (2013.01); *G06N 7/005* (2013.01); *G16C 20/30* (2019.02); *G16H 10/20* (2018.01); *G16H 50/20* (2018.01); *G16H 70/40* (2018.01)

(56) References Cited

U.S. PATENT DOCUMENTS

| | | |
|---|---|---|
| 2014/0039911 A1 | 2/2014 | Iyer |
| 2014/0058744 A1 | 2/2014 | Nadarajah et al. |
| 2015/0363553 A1 | 12/2015 | Rustgi et al. |
| 2016/0048655 A1 | 2/2016 | Maitra et al. |
| 2017/0262609 A1* | 9/2017 | Perlroth ................. G16H 10/20 |

FOREIGN PATENT DOCUMENTS

| | | |
|---|---|---|
| WO | WO 2015/087140 A1 | 6/2015 |
| WO | WO 2016/046744 A1 | 3/2016 |

OTHER PUBLICATIONS

Nováček et al., "Linking the Scientific and Clinical Data with KI2NA-LHC—An Outline," in Proc. 26th IEEE Intl. Symp. Computer-Based Med. Sys. 540-41 (2013). (Year: 2013).*
Wu et al., "Exploiting Online Discussions to Discover Unrecognized Drug Side Effects," in 52.02 Methods of Info. Med. 152-59 (2013). (Year: 2013).*
Karimi et al., "CADEC: A Corpus of Adverse Drug Event Annotations," in 55 J. Biomedical Informatics 73-81 (2015). (Year: 2015).*
Hamed et al, "Twitter K-H Networks in Action: Advancing Biomedical Literature for Drug Search," in 56 J. Biomedical Informatics 157-68 (2015). (Year: 2015).*
Liu et al., "Role of Text Mining in Early Identification of Potential Drug Safety Issues," in Biomedical Literature Mining 227-51 (Kumar et al. eds., Humana Press, 2014). (Year: 2014).*
White et al., "Web-Scale Pharmacovigilance: Listening to Signals from the Crowd," in 20 J. Am. Med. Informatics Assoc. 404-08 (2013). (Year: 2013).*
Metke-Jimenez et al., "Concept Extraction to Identify Adverse Drug Reactions in Medical Forums: A Comparison of Algorithms," in arXiv preprint arXiv:1504.06936 (2015). (Year: 2015).*
Burger et al., "Social Media Communications Networks and Pharmacovigilance: SequelAE-2.0," in 2013 IEEE 15th Intl. Conf. e-Health Networking, Applications and Servs. 1-3 (2013). (Year: 2013).*
Karimi et al., "Text and Data Mining Techniques in Adverse Drug Reaction Detection," in 47.4 ACM Computing Surveys 56 (2015). (Year: 2015).*
German Search Report dated Sep. 6, 2016 in corresponding German Patent Application No. 102016207473.3.
British Office Action dated Sep. 23, 2016 in corresponding British Patent Application No. 1607496.5.
Extended European Search Report dated Sep. 26, 2017 in corresponding European Patent Application No. 16203856.6.
White R. W. et al.: "Toward Enhanced Pharmacovigilance Using Patient-Generated Data on the Internet," Clinical Pharmacology and Therapeutics, vol. 96, No. 2, Apr. 8, 2014, pp. 239-246, XP055407660.
Yates A. et al.: "Extracting Adverse Drug Reactions from Social Media," Proceedings of the Twenty-Ninth AAAI Conference on Artificial Intelligence, AAAI 15, Jan. 25-30, 2015 Austin, Texas, USA, Jun. 2015, pp. 2460-2467, XP009500243.
Sarker A. et al.: "Utilizing social media data for pharmacovigilance: A review," Journal of Biomedical Informatics, vol. 54, Feb. 23, 2015, pp. 202-212, XP055407654.
Sarker A. et al.: "Social Media Mining for Toxicovigilance: Automatic Monitoring of Prescription Medication Abuse from Twitter," Drug Safety, vol. 39, No. 3, Jan. 9, 2016, pp. 231-240, XP055407658.
Henegar C. et al.: "Building an ontology of adverse drug reactions for automated signal generation in pharmocovigilance," Computers in Biology and Medicine, New York, NY, US, vol. 36, No. 7-8, Jul. 1, 2006, pp. 748-767, XP028025081.
Sir M. et al.: "Ontology versus Database," IFAC-PapersOnLine, vol. 48, No. 4, Jan. 1, 2015, pp. 220-225, XP055407664.
Communication pursuant to Article 94(3) EPC dated Oct. 21, 2020 in related European Patent Application No. 16203856.6 (12 pages).
Koutkias, V. et al. (2015) "*A Multiagent System for Integrated Detection of Pharmacovigilance Signals*"; Journal of Medical Systems, vol. 40, No. 2, article nr 37, pp. 1-14, DOI: 10.1007/S10916-015-0378-0, (XP035918503) (12 pages).

* cited by examiner

SYSTEM AND METHOD TO PRODUCE AND VALIDATE WEIGHTED RELATIONS BETWEEN DRUG AND ADVERSE DRUG REACTIONS

CROSS-REFERENCE TO RELATED APPLICATIONS

This application claims the benefit of UK Application No. 1607496.5, filed Apr. 29, 2016, in the UK Intellectual Property Office and German Application No. 102016207473.3, filed Apr. 29, 2016, in the German Patent and Trademark Office, the disclosures of which are incorporated by reference herein.

BACKGROUND

1. Field

The present invention relates to identification of the risks associated with adverse drug reactions to drugs (which in this context are taken to include healthcare products/pharmaceuticals/medicaments of all types).

2. Description of the Related Art

The term adverse drug reaction (ADR) refers to injuries, disorders or discomfort caused by medical intervention related to the use of a drug. Such reactions are non-beneficial effects that can result in either temporary or permanent defects, potentially leading to restriction to "normal" biological and/or mental functions. ADR can be detected in different ways:
1. Through chemical and pharmacodynamics studies when the drug (or its administration channel and administration protocols) was designed and manufactured.
2. Through different phases of clinical trial when controlled studies are carried out and data are collected and analysed.
3. Through monitoring patients when the drug is put into practical use.

Among all the above, a high risk and maximum difficulty is experienced when the drug is actually in use. This is due to the following reasons:
1. It is hard to collect large scale drug reaction data to determine whether a drug should be put on the alert list. Deploying such a large scale monitoring network requires coordination among authorities from different national regions and/or even different countries.
2. Even if a large-scale monitoring collaboration can be established, delay in feedback through such official channels can mean that more patients (living subjects, whether human or animal to whom the drug is administered) could be at risk when data are collected before the initial warning can be raised.
3. Some ADRs may not be reported and thus not officially documented. This can be due to the low degree or short duration of discomfort for patients experiencing such ADRs. However, this does not rule out the possibility that a more serious reaction can occur.

Invention embodiments aim to alleviate the difficulties of determining ADRs associated with drugs that are already in widespread use (although they could also be used at a public trial stage).

SUMMARY

According to an embodiment of a first aspect there is provided a system to produce and validate weighted relations between drugs and ADRs, the system comprising: a public data monitoring module to monitor social media for links between drugs and ADRs; a knowledge extraction module to extract a relation between a drug and an ADR using named entity recognition and to provide a weighted relation between the drug and the ADR based on confidence of the link between the drug and the ADR in the social media; a local knowledge base to store the relation with its weight; a relation refinement module using domain knowledge in an ontology database to refine the weighted social media relation in accordance with one or more ontologies of drug names and of ADR symptoms; a quantification ADR module to further quantify the weighted social media relation by using drug and ADR links extracted from research publications and/or from clinical trial reports and providing a research weight for the relation, and/or to quantify the weighted social media relations by using an internet search engine and searching for the drug and the ADR, where a number of hits quantifies an internet weight for the relation.

This system can detect adverse drug reactions that may not be picked up in official drug instructions or during clinical trial. Invention embodiments collect information such as complaints from social media (public forums, websites and applications that enable users to create and share content or to participate in social networking and thus provide real time information exchange on the World Wide Web) expand the search using semantic technology (ontologies), confirm and hence validate the complaints with broader information gathering, treating the internet and/or publications and reports as a source of knowledge, and quantify the results to reflect confidence levels.

The system may produce a graph and/or individual relations which can be displayed. User queries can be entered.

In one embodiment, the knowledge extraction module provides the weighted relation between the drug and the ADR as a triple in the form <drug, ADR, c> where c is the confidence level. This use of triples is suitable for storage as a graph.

The relation refinement module can allow expansion of the relation. For example the original relation can be expanded to include equivalent drug names and symptoms. These equivalents are variations, which may be stored together with the original. Equally, refinement of the relation may replace an ADR symptom with a more or less specific ADR symptom.

In some embodiments, only social media relations having a social media weight above a threshold confidence level are retained. Thus relations below this confidence level are not stored in the local knowledge base or processed further.

The quantification ADR module can use the research weight and/or the internet weight to adjust the social media weight. Alternatively all the weight types can be stored separately, for example in the format <drug, ADR, (source1, weight1; source2, weight2 ... )>

The quantification ADR module can compute the research weight based on the ratio of evidence support linking (mentioning) the drug and the ADR to the overall mentions of the drug.

The quantification ADR module can compute the internet weight based on a search engine distance between the drug and the ADR.

Some embodiments provide a correlation scoring module that computes the confidence of the relation by aggregating the social media weight, the research weight and the internet weight. A user-defined strategy may give a weighting to any of the social media weight, the research weight and the internet weight.

In some embodiments, the monitoring is not limited to drugs and ADRs, but can also monitor for links between drugs and other substances (any substance which is not the particular drug in question). In this case, for example, the public data monitoring module is also to monitor social media for links between drugs and other substances; the knowledge extraction module is also to extract a relation between a drug and another substance using named entity recognition and to provide a weighted relation between the drug and the other substance, the weight based on confidence of the link between the drug and the other substance in the social media; the local knowledge base is also to store the drug-substance relation with its weight; the relation refinement module is also to use the ontology database to refine the weighted social media drug-substance relation in accordance with one or more ontologies of drug names and/or of other substances; and the quantification ADR module is also to further quantify the weighted social media drug-substance relation by using substance and drug data extracted from research publications and/or from clinical trial reports and providing a research weight for the drug-substance relation, and/or to quantify the weighted social media drug-substance relation by using an internet search engine and searching for the drug and the ADR, the number of hits quantifying an internet weight for the drug-substance relation.

Further embodiments of the invention allow for a user query system to allow a user to assess relations between drugs and ADRs. This system can comprise:

the system to produce weighted relations as described above, with the addition of: a user interface allowing input of a user query and output of a query result; a query expansion/rewriting module using the domain ontology to rewrite the query; and a query processing module to process the user query, for example into an internal query representation and to retrieve answers from the local knowledge base.

In the user query system, if no relation is found in the local knowledge base to answer the query, the system may be arranged to carry out public data monitoring in real time.

According to an embodiment of a method aspect, there is provided a method of producing and validating weighted relations between drugs and ADRs comprising: monitoring social media for links between drugs and ADRs; extracting a relation between a drug and an ADR using named entity recognition and providing a weighted relation between the drug and the ADR based on confidence of the link between the drug and the ADR in the social media; using domain knowledge in an ontology database to refine the weighted social media relation in accordance with one or more ontologies of drug names and/or of ADR symptoms; quantifying the weighted social media relation by using ADRs extracted from research publications and/or from clinical trial reports and providing a research weight for the relation; and/or quantifying the weighted social media relations by using an internet search engine and searching for the drug and the ADR, numbers of hits quantifying an internet weight for the relation.

According to an embodiment of a further method aspect, there is provided a method of allowing a user to query for a link between a drug and an ADR comprising: allowing input of a user query; processing the query; using the domain ontology to rewrite the query; and retrieving a query answer from the quantified weighted social media relations produced according to the method described above.

The system (apparatus) according to preferred embodiments is described as configured or arranged to, or simply "to" carry out certain functions. This configuration or arrangement could be by use of hardware or middleware or any other suitable system. In preferred embodiments, the configuration or arrangement is by software.

Thus according to one aspect there is provided a program which, when loaded onto at least one computer, configures the computer to become the system according to any of the preceding system definitions or any combination thereof.

According to a further aspect there is provided a program which when loaded onto the at least one computer configures the at least one computer to carry out the method steps according to any of the preceding method definitions or any combination thereof.

In general the computer (or a network of computers) may comprise the elements listed as being configured or arranged to provide the functions defined. For example this computer may include memory, processing, and a network interface.

The invention can be implemented in digital electronic circuitry, or in computer hardware, firmware, software, or in combinations of them. The invention can be implemented as a computer program or computer program product, i.e., a computer program tangibly embodied in a non-transitory information carrier, e.g., in a machine-readable storage device, or in a propagated signal, for execution by, or to control the operation of, one or more hardware modules. A computer program can be in the form of a stand-alone program, a computer program portion or more than one computer program and can be written in any form of programming language, including compiled or interpreted languages, and it can be deployed in any form, including as a stand-alone program or as a module, component, subroutine, or other unit suitable for use in a data processing environment. A computer program can be deployed to be executed on one module or on multiple modules at one site or distributed across multiple sites and interconnected by a communication network.

Method steps of the invention can be performed by one or more programmable processors executing a computer program to perform functions of the invention by operating on input data and generating output. Apparatus of the invention can be implemented as programmed hardware or as special purpose logic circuitry, including, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions coupled to one or more memory devices for storing instructions and data.

The invention is described in terms of particular embodiments. Other embodiments are within the scope of the following claims. For example, the steps of the invention can be performed in a different order and still achieve desirable results. Multiple test script versions can be edited and invoked as a unit without using object-oriented programming technology; for example, the elements of a script object can be organized in a structured database or a file system, and the operations described as being performed by the script object can be performed by a test control program.

Elements of the invention have been described using the terms "module" and "unit" and functional definitions. The skilled person will appreciate that such terms and their equivalents may refer to parts of the system that are spatially separate but combine to serve the function defined. Equally, the same physical parts of the system may provide two or more of the functions defined.

For example, separately defined means may be implemented using the same memory and/or processor as appropriate.

BRIEF DESCRIPTION OF THE DRAWINGS

Preferred features of the present invention will now be described, purely by way of example, with references to the accompanying drawings, in which.

DETAILED DESCRIPTION

Figure 1:
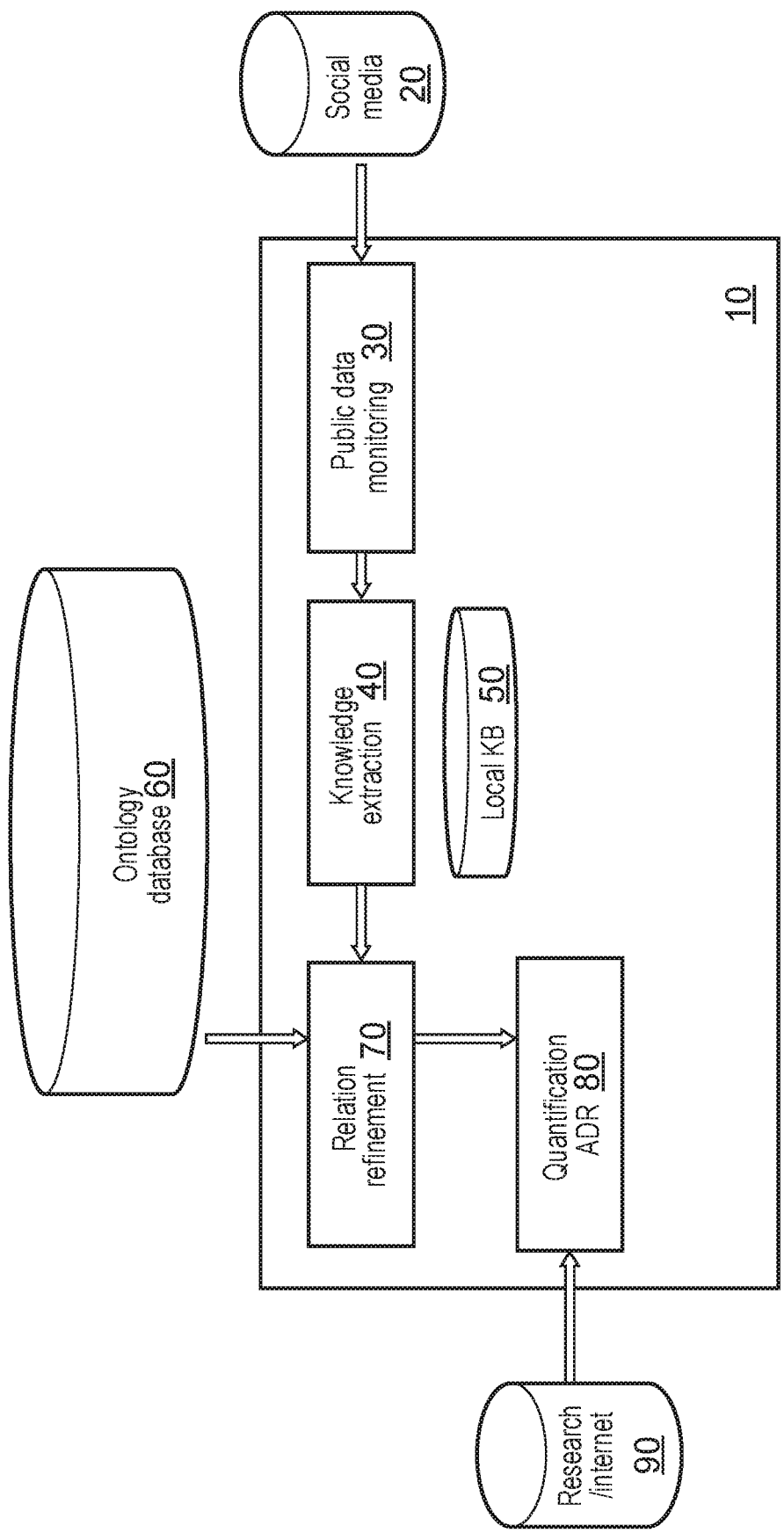
FIG. 1 is a block diagram of components in a general embodiment of the invention.

FIG. 1 shows a general system embodiment producing and quantifying (validating) weighted relations between drugs and ADRs.

The system includes a public data monitoring module 30 which monitors social media (such as TWITTER social media, etc. and including public data forums) for links between drugs and ADRs. There is also a knowledge extraction module 40 which uses this monitoring to extract a relation between a drug and an ADR using named entity recognition (and relation extraction techniques) and provides a weighted relation between the drug and the ADR based on confidence of the link between the drug and the ADR in the social media. A local knowledge base stores the relation with its weight (local storage may also be available to store interim results, etc.). For example the relation may be stored in the form <drug (d), ADR (s), confidence (c)>. A relation refinement module 70 uses at least one ontology database 60 containing domain knowledge (the database is probably situated outside the system) to refine the weighted social media relation in accordance with one or more ontologies of drug names and of ADR symptoms. These ontologies are stored within the database 60. A quantification ADR module 80 can further quantify the weighted social media relation by using drug and ADR links extracted from research publications and/or from clinical trial reports 90 and providing a research weight for the relation. The quantification ADR module can alternatively or additionally quantify the weighted social media relations by using an internet search engine and searching for the drug and the ADR, numbers of hits (for example for d, s and s+d, together) being used to quantify an internet weight for the relation.

This figure does not show user query components. These may include a user interface allowing input of a user query (for example in a natural language) and output of a query result; a query expansion/rewriting module using the ontology database to rewrite the query; and a query processing module to process the user query into an internal query representation and to retrieve answers from the local knowledge base.

The system can be queried remotely (for example using a network interface) or locally via a Graphical User Interface (GUI), for example. For these purposes the query processing module may be provided, which can access the local knowledge base and can potentially also make use of the refinement module which is in this case used to refine both extracted relations and also queries by using semantic processing. Otherwise, a separate query expansion/rewriting module may be provided.

The results of a user query can act not just as general information, but also as a diagnosis, or could even raise an alarm. The results can also be exported for use in other system.

In practice, knowledge/relations learned from social media can serve in one of the following ways. Firstly, if the social media confidence level is high while the significance/confidence values drawn from internet and/or research are relatively low, such discrepancies might indicate a new ADR for a particular drug which should be investigated and this can give rise to an alert to the authorities and pharmaceutical industries to review their clinical research. Alternatively, the additional ADR can be added as part of a diagnostic assistant for a medical practitioner. For instance, it can be deployed alongside other information in a system such as the current hospital information system or a general practice information system. When doctors and other practitioners (including, for example, vets, and nurse practitioners) decide to prescribe a drug, both established information and the social media-based information can be displayed together to enable the practitioner to make informed and evidence-based decisions.

Secondly, when there is an agreement between social media and research-based knowledge and a disagreement between them and existing drug manuals/instructions, a potential drug call-back case might be established. In this case, the system can (potentially even automatically) make a submission to national authorities, e.g. through FDA or NICE Yellow Card Scheme, providing evidence for further investigation.

Thirdly, the social media based drug-ADR relations can be stored in a database and periodically compiled to be consumed by the industries for quality assurance and pharmacovigilance research—comparing and contrasting with their ADR data repository and aggregating the scores with established numeric correlations between drugs and ADRs. Finally, authorities can accumulate such data and set up an alert mechanism: once the accumulated scores reach a predefined threshold, review of ADRs of a drug will be performed and it is decided whether medical guidelines should be revised accordingly.

Figure 2:
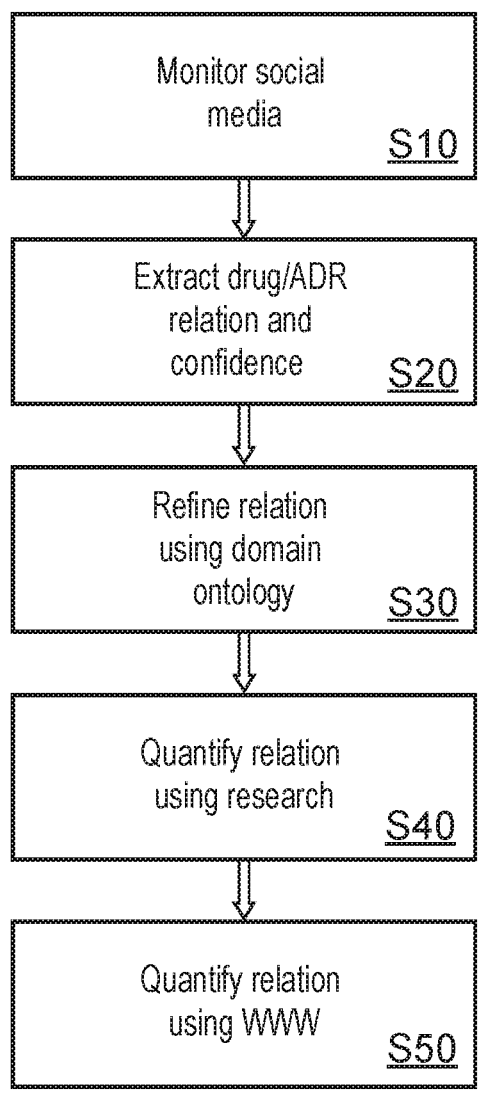
FIG. 2 is a flow chart of a method in a general embodiment.

FIG. 2 is a flow chart of a general invention embodiment. In step S10 social media is monitored. In step S20 this monitoring is used to extract a drug/ADR relation and a weighting based on confidence. In step S30 the relation is refined using one or more domain ontologies (specific to the area(s) of drugs and/or symptoms). This can allow the relation to be reworded or to be expanded to give relations including synonyms and variations of the original relation. These variations may all be allocated the same weight as the original relation, or further access to social media could derive an individual weight for each relation.

In step S40, the relation (and each of the variations) is quantified using research. Additionally or alternatively in step S50, the relation (and each of the variations) is quantified using the internet. The term "quantification" is used here to include providing a weight or confidence level based on a source which by its nature may be more reliable than the social media, either in terms of breadth of input (the internet) or in terms of expertise (research papers, trials etc.).

Figure 3:
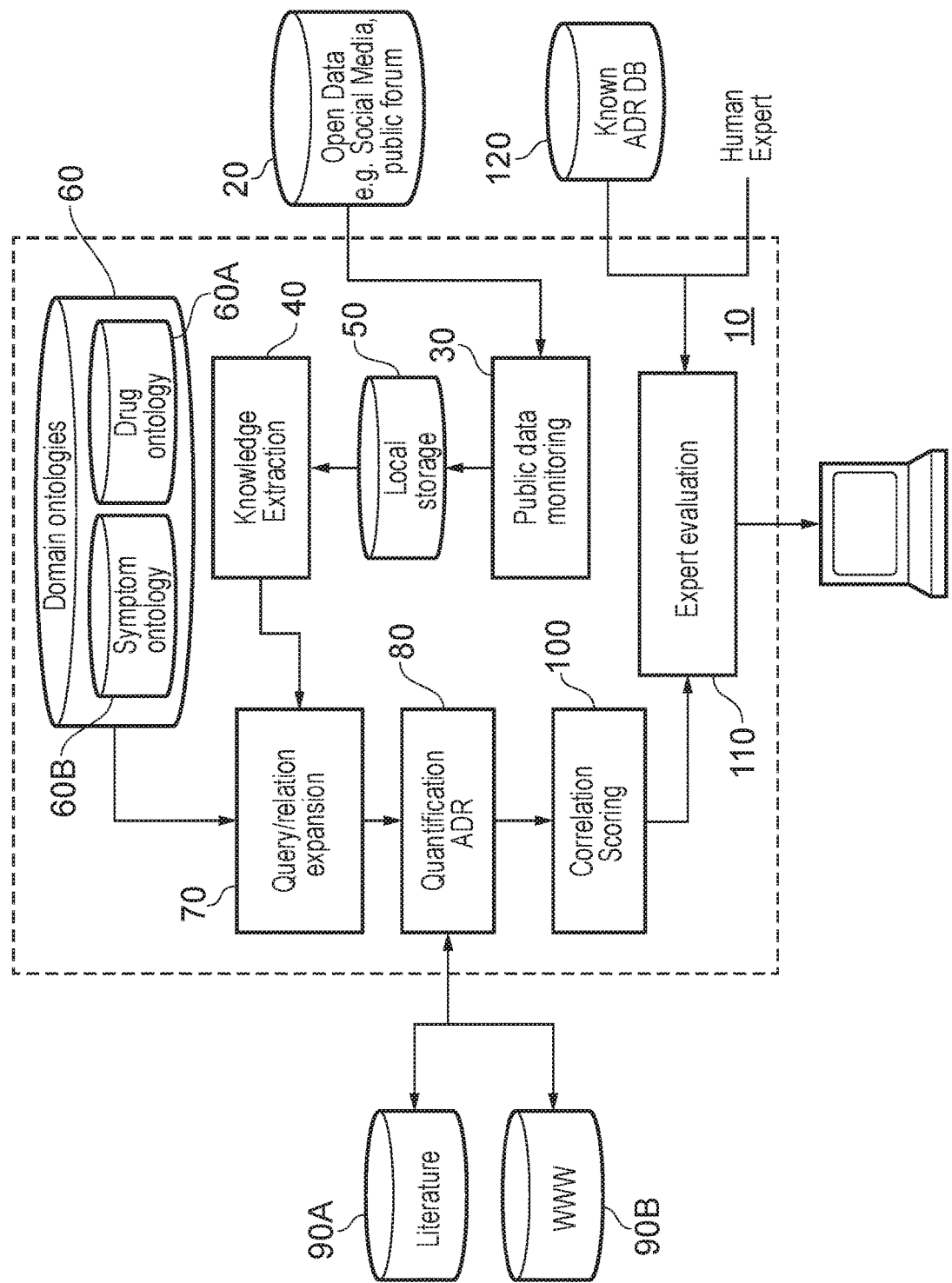
FIG. 3 is a block diagram of the main system components in a detailed embodiment.

FIG. 3 shows a block diagram of the main system 10 components in a detailed embodiment.

Key data sources include:
1. Medical literature 90A.
2. World Wide Web 90B as main knowledge repository. The access to WWW is facilitated by Internet Search Engines (ISEs).
3. Social media 20.
4. Existing ADR Database, e.g., 120 Drug Bank
5. Human experts 110 who play a critical role here in terms of providing domain knowledge and validating automatically detected results.

The system contains the following components/modules to produce and validate the weighted relations, which may then be queried by a user:

Public Data Monitoring 30 which can pull data and changes from the public domain 20 (comparing to a local copy in local storage 50 for relations between drugs, and ADRs and confidence level of the relations);

Knowledge/Information Extraction 40, that extracts and tracks drug related complaints from main social media sites, possibly based on the locally stored data;

Remote access to domain ontologies 60 including drug ontology 60A and system ontology 60B that provide knowledge on text analysis and search queries. The ontologies can be used to expand an end user query which e.g. can be of any of the following forms: 1. A brand name of a drug; 2. A generic name of a drug; 3. Combination of a drug name and a disease name. They can also be used to refine a relation extracted from social media as explained in more detail by the following:

A Relation refinement 70 that leverages domain knowledge to refine the relations extracted from social media and/or potentially also to either expand or sometimes narrow down user queries.

A Quantification ADR 80 that uses literature 90A and/or internet data 90B to estimate the confidence level (in the form of a numerical weight) of a relation based on these sources (as opposed to a confidence level based on social media) and validate the relations.

A Correlation scoring 160 that computes the overall confidence of the suspected ADR taking into account the different sources.

A Expert evaluation 110 that checks the results against either a known ADR database 120 or based on human expert inputs.

Technical Details:

The system and method of invention embodiments can be broken down into several steps which are detailed as follows.

Public data monitoring and information extraction:

Social media has an ever growing influence in many areas of life, work, and entertainment in modern societies. The main assumptions used in this embodiment are that:
1. A large amount of users (possibly of different kinds of social media) share their latest status (physical and mental) with others (in a way that is either exclusive to a group of people, e.g. friends or families, or openly with the general population).
2. When sharing, people frequently update their status on social media.
3. With sufficient population, noise and false information can be either detected or corrected by authentic information.

Social media monitoring in this embodiment can utilize established text analysis techniques (including named entity recognition and potentially also linguistic patterns) to detect drug names and key symptoms and complaints. For instance, "BACTRIM medicine gives me headache" or "had BACTRIM medicine . . . very bad headache" can be a main message on social media. NER (named entity recognition) technology can help to identify "BACTRIM" as the name of the medicine and "Headache" as the key complaint.

In this embodiment, off-the-shelf NER tools and libraries can be used. Such tools take text data as input, parse the text using predefined entity dictionary(ies) and label detected as well as classified entities. For instance, if example text "Parkinson's can be alleviated by . . . administration of the lDOPA drug" is fed into an NER tool, the output will be "<disease>Parkinson's</disease> can be alleviated by . . . administration of <drug>lDOPA</drug>". Such labelling sometimes is accompanied by numeric confidence values. Currently there are well-curated general purpose NER dictionaries and special ones for different domain. In the above example, a special dictionary in the medical domain (for disease and drug name recognition) is used.

Other NLP (Natural Language Processing) techniques which may be used include stemming (unifying different forms or tenses of words), plural folding (removing plural form of words), stop word removal (removing common words, such as "a", "and", "or", etc., again, based on predefined checklists), etc. Off-the-shelf NLP tools and libraries can be used (for instance Stanford NLP).

One or more medical-domain specific ontologies of drugs and more general medical interventions stored in one or more ontology databases can be used to define, disambiguate, and reconcile names. An ontology can also capture domain knowledge of symptoms and complaints. Such ontologies can come from existing ontology repositories such as OBO (Open Biomedical Ontologies) or are designed from scratch with help from medical experts.

This module, and indeed the whole system, can be extended beyond drug adverse reaction. For instance, relations among drugs and other substances (that are not the drug in question) such as between two drugs, between a drug and other supplements, between a drug and food and between a drug and any other substances can be extracted to provide a complete picture concerning drug safety and drug administration.

In order to generalise the system to include further relations, essentially the same process as for the drug-ADR relation must be carried out again, using specific ontologies for the new relation and adapting some other modules. For example, the following steps could be used. Firstly specific data sets should be queried or crawled. Secondly, new NER dictionaries should be compiled or obtained to enable the detection of specific types of entities. The relations among entities can then be computed as before as statistical associations between recognized entities.

When extracting drug names and symptoms, established linguistic patterns can be used to differentiate between negative and positive relationships. For instance "Headache after taking Bactrim" and "headache gone, after taking Bactrim" can be differentiated to indicate the connection between drug and symptoms. Existing NLP techniques can be used to detect whether a statement is a negation or confirmation. Also, it is important to differentiate direct and indirect relationships. For instance, "took bactrim, headache" and "took Bactrim, the game gets me headache" are giving different causal relationships. In this case, a "window" or "distance" should be defined to constrain how far apart the identified terms should be. The exact NLP techniques that can be applied in the above two cases are beyond the scope of this document. Nevertheless, for key languages such as English, established NLP can be applied.

Outcomes of social media monitoring can be formalized as a triple, where d is the name of the drug and s the name of the symptom (ADR); c indicates the confidence of such a relation.

$$<d,s,c>$$

Due to a lack of quality assurance of social media data, the system can assign each captured relation a confidence value. It will only proceed to the next step of storing the relation in local storage when the confidence is above a threshold. There are many ways to compute the confidence. The following approach is only an exemplary one.

$$c = \sum -\log\left(\frac{\#\langle d, s\rangle_t + \alpha}{\#\langle d\rangle_t + \#\langle s\rangle_t + \beta}\right) \cdot e^{-\lambda t}$$

Where:
$\alpha$ and $\beta$ are arbitrary coefficients that set the value of the fraction as well as the denominator to be non-zero values.
t is a given time point prior to the current time
$\lambda$ is to adjust the curve of time decaying factor
$\#\langle d, s\rangle_t$ is the number of instances with d and s in a time period t
$\#\langle d\rangle_t$ is the number of instances of d in a time period t
$\#\langle s\rangle_t$ is the number of instances of s in a time period t In this method, given a specific time window, the confidence is the ratio of number of mentions to the total number of data items (e.g. tweets). The time window is split into different fragments and the overall confidence is the sum of the ratios of all fragments adjusted by an exponential decaying factor. Note that the overall confidence is not necessarily between 0-1. But this number can be normalised against a popular benchmark topic to bring the value into 0-1 as follows, where topic is an arbitrary popular topic to gauge the popularity of the joint topic of D and S.

$$\overline{c} = \frac{c(d, s)}{c(\text{topic})}$$

The outcome of this step is a domain knowledge graph where nodes are drugs and adverse drug reaction symptoms and edges connect drugs and potential symptoms. It will only accept relations when the confidence value is above a potentially user-defined threshold. The edges are labelled with numeric confidence values indicating the strength of the drug-symptom connection.

This is a domain knowledge model (graph) extracted from public data sources known as social media. It is different from existing ontologies, but can rely on existing ontologies to improve quality and performance, as set out below. Only relations above a certain threshold will be stored. Depending on data sources, it is possible to maintain separate knowledge models (graphs) for different sources for data safety and quality reasons.

A Query/Relation expansion function of the relation refinement 70:

The term "domain ontology" or "ontology" is used herein to refer to ontologies which are manually defined and well-curated with significant involvement of domain experts. These ontologies are considered as ground truth (accepted as correct in the system) and can help relation extraction from un-curated data sources, as well as use query improvement.

Relations extracted from public data sources can sometimes be very unspecific and/or ambiguous. In this case, ontology can be used to present more specific results for better end-user/expert response. For instance, from public data sources, a relation can be established between naproxen and ulcer. Using ontologies, a relation can be refined as "naproxen, stomach ulcer", etc. to allow better filtering and screening.

Figure 4:
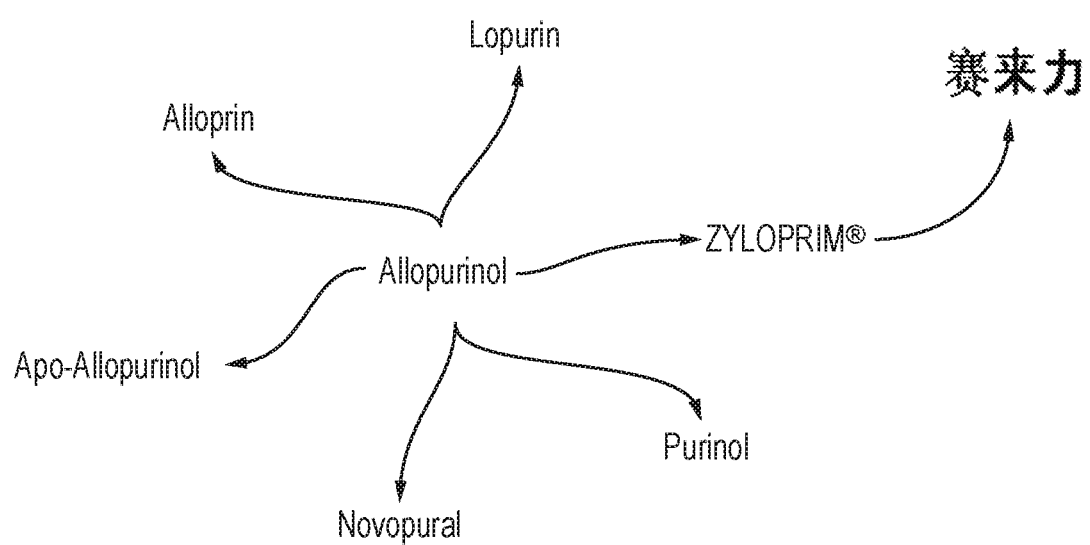
FIG. 4 is a conceptual diagram of generic and brand drug names for ALLOPURINOL.

Identified symptoms and drugs (in either or both of user queries and extracted relations) can be subject to knowledge refinement. Ontologies are used to broaden and/or narrow the extracted topics/keywords. The rationale behind such rewriting is that drugs are normally sold and mentioned by their brand name while different companies distribute the same drug with different brand names. By using semantic technology, new queries (internal queries) can be generated against different brands of the same drug and/or against the generic names. For instance, FIG. 4 shows the correspondence of generic names and brand names:

In this example, Allopurinol is manufactured and marketed under different names (in different languages). Also there are clear hierarchies between brand names as well as between drugs (due to the resemblance of their chemical structures). A drug ontology can encode all the relationships and drug-drug relationships in a computer understandable language, for semantic processing.

This expansion of user queries and extracted relations is hence often based on manually crafted and curated ontologies. Such ontologies are normally outcomes of community wide collaborations and efforts. They are considered groundtruth. Relations extracted in invention embodiments from (public) data sources representing social media are considered knowledge that are yet to be fully verified but can complement the ground truth knowledge.

Similarly, for ADRs which are symptoms including signs which are perceivable changes in function, sensation and/or appearance due to medical intervention of diseases, semantic technologies can help to fine tune the symptoms to generate a more targeted search. For instance, a symptom ontology, such as those found at biolontology.org, can be used to replace a symptom with a more generic one to broaden the search or a more specific one to remove noise data. The broadening and narrowing down of symptoms (for example) is carried out by the system based on "groundtruth" ontologies. It is not necessary for it to be transparent to end users.

ADR Quantification

Social media, though gaining popularity, is only used by a subpopulation. In order to gain more balanced results, other sources of information are used. This component tries to confirm or reject the extracted relationship by examining it in the context of: 1, established and quality assured medical publications (e.g. research publications) and/or 2, the entire WWW (World Wide Web or internet). The assumptions are as follows. Firstly, medical publications normally are based on well-designed studies with carefully recruited test populations. They should help to increase or decrease the confidence of the extracted connections between drugs and symptoms. Secondly, information collected from WWW will be sufficiently representative and unbiased (in the form of news articles, blogs, bulletin-boards, discussion forum, and many other textual representations) to give a faithful reflection of large direct or indirect information providers regarding the connections between drugs and complains (symptoms and signs as ADRs).

Figure 5:
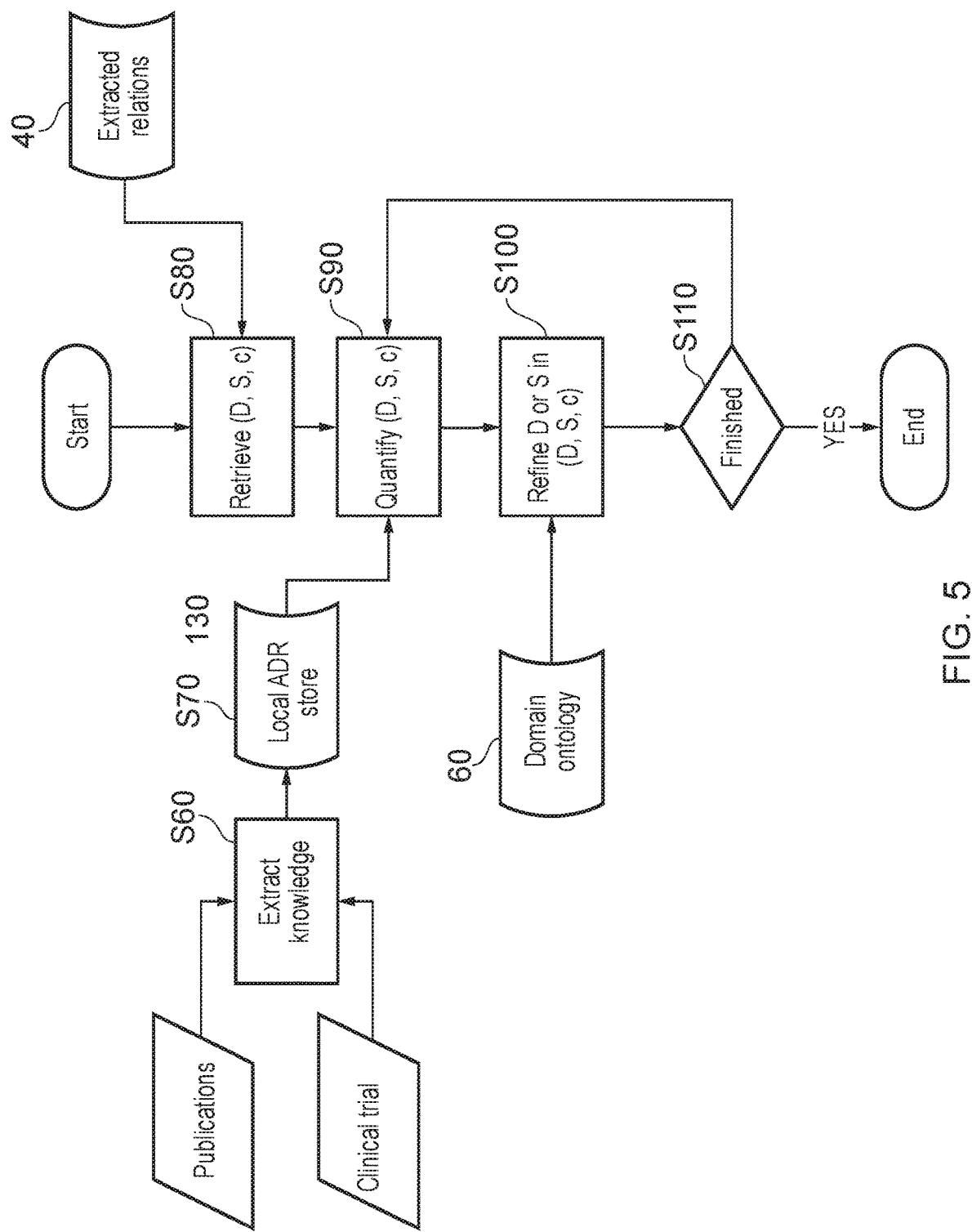
FIG. 5 is a block diagram of the quantification ADR module.

FIG. 5 explains a specific embodiment of the quantification ADR module functionality for literature based quantification. It stores relations, S70, in a local ADR store 130, which may in fact use the same memory as knowledge base 50.

Periodically, established linguistic patterns are used to extract drug/ADR relations from research publications and from published clinical trial reports, both categorised as research. Exact linguistic patterns can be based on existing research and studies. The extracted relations based on research are treated as ground truth and stored in a local ADR store. Newly discovered (d, s) from social media are retrieved S80, the process iterating through a set of relations so that each is evaluated individually, and quantified S90 based on these research relations. The quantification can be computed as the overall ratio of evidence support #|adr(d, s)| to the overall mentioning of a drug #|adr(d,*)| in the research.

Furthermore, both the drug and symptom can be refined S100 based on domain ontology database 60, although the social media relations can remain unchanged, for traceability. For instance, drugs can be replaced with their generic name and other brand names to extract apparently irrelevant ADRs, using the query/relation expansion previously described. Symptoms can be replaced by synonyms or largely similar symptoms but with different descriptions.

The refinement process continues until all the alternatives introduced by the domain ontology database have been exhausted. "Finish" at S110 refers to whether s or d can be further refined based on "ground-truth" domain ontologies.

The overall quantification can be a weight aggregation of the original (d, s), the drug adjusted one, and the symptom adjusted one.

In summary, all the relations extracted from social media are for example stored in a graph. Such graphs (including edges and edge weights) are subject to further refinement using more trust-worthy data from publications and trial reports.

Quantification with WWW

WWW quantification can be performed using internet search engines (ISE). The social media relations which are up-to-date, real-time relations refined in the relation/query expansion module will be sent to ISE. The number of hits will be used to decide whether d and s are highly correlated. This is done as follows in one specific embodiment:

1. Generate ISE queries of the following: joint search query containing both d and s, search query d and search query s 2. Compute Search Engine Distance as $$SED(d, s) = \frac{\max(\log \text{hit}(d), \log \text{hit}(s)) - \log \text{hit}(d, s)}{\log N - \min(\log \text{hit}(d), \log \text{hit}(s))}$$

This is borrowed from a Normalized GOOGLE Distance search engine distance from ("The Google Similarity Distance," Rudi L. Cilibrasi and Paul M. B. Vitányi, IEEE Transactions on Knowledge and Data Engineering, Vol 19, No. 3, March 2007, 370-383).

As the minimum value between the two logarithm values is likely to be the one of drug name and a comparing to N, which is the number of all indexed pages, the second part of the denominator is very small, the above equation can be simplified to $$SED(d, s) = \frac{\max(\log \text{hit}(d), \log \text{hit}(s)) - \log \text{hit}(d, s)}{\log N}$$

3. Based on the domain ontology of symptoms, other possible drugs/ADRs can be retrieved to generate internal queries:

$$SED(d, s') = \frac{\max(\log \text{hit}(d), \log \text{hit}(s')) - \log \text{hit}(d, s')}{\log N},$$

where $s' \in O(s)$

O(s) is the entire set of ADR symptoms based on an ontology. A similar expression applies for drugs.

4. A normalized quantification (confidence) of symptom s is then computed as $$c(d, s) = \frac{SED(d, s)}{\sum_{s' \in O(s)} SED(d, s')}$$

In this case, the common denominator log N can be removed. This is essential as the total number of indexed pages varies from search engine to search engine and varies along time.

Figure 6:
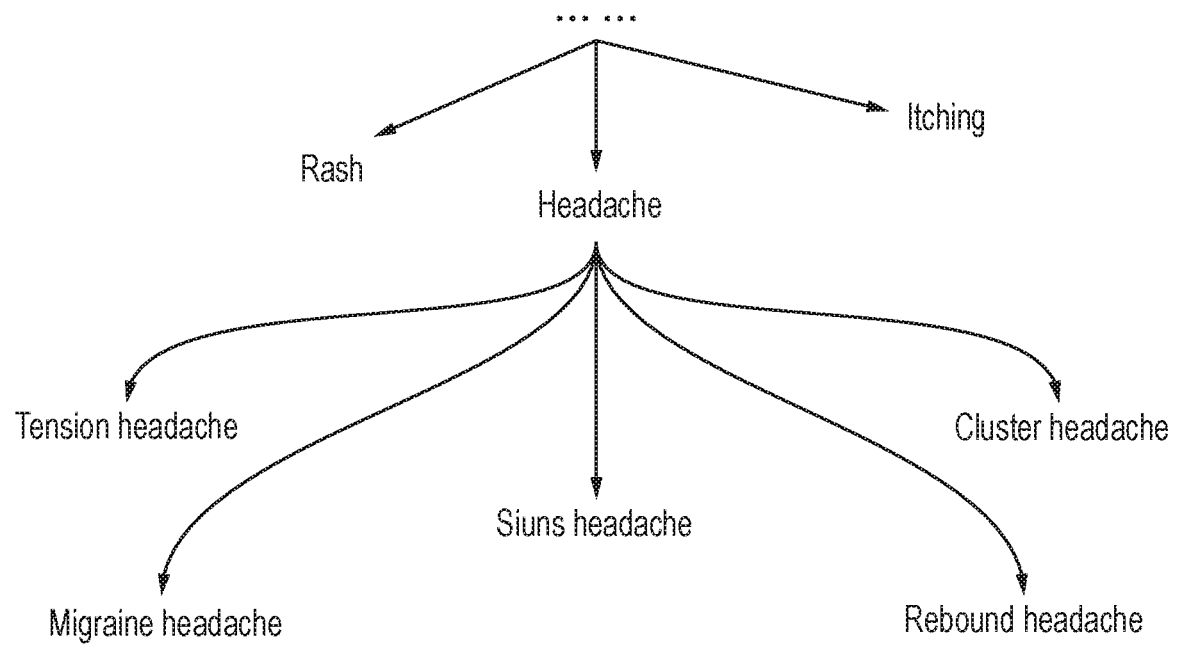
FIG. 6 is a hierarchical diagram showing different levels of symptoms.

When there are more than one level of symptom hierarchy, e.g. as shown in FIG. 6, the subtypes of a symptom (headaches) will not be used to quantify the confidence. Instead, other symptoms at the save conceptual level as headache will be used—in this case "itching" and "rash".

Correlation Scoring 100

User queries (normally a drug name) trigger retrieval or extraction of relations (d, s). The extracted (d, s) needs to be verified and refined using more trust-worthy sources. The correlation module in this embodiment can aggregate those scores from different sources (and confidence computation modules), potentially taking user input into account. Of course it is alternatively possible to simply present a drug/ADR relation with different confidence values linked to different sources to the user.

Correlation refers to the connections between a drug/medicine and a symptom/ADR. The aggregation can be a simply weighted aggregation in which users or an overall standard setting specify the trustworthiness value of each scoring approach. It can also be based on a more complicated learning approach, in which the weight of the contribution from each module is dynamically assigned based on a user defined strategy. Here, a simple weighted aggregation is used as an example:

$$c_{overall}(d,s) = \Sigma c_i(d,s) \cdot \omega_i$$

$\omega_i$ is the weight assigned to different data sources that are used to confirm or refine the extracted relation.

Expert Evaluation 110

The proposed system according to an invention embodiment can automatically extract ADRs of drugs based on social media inputs. However, the generated drug-symptom correlations may still be subject to human inspection to ensure quality. This is not a mandatory function. When present, the Expert Evaluation module can present the extract correlations, together with both overall confidence value and the individual confidence values. So the domain experts can make their judgement accordingly. A GUI can be provided to enable such communication and interaction.

The confidence values/expert input may be for the entire graph, of just for selected links, this depends on the capacity and availability of domain experts. If the data are not likely to be huge, it is possible to present the entire graph of extracted and refined relations to the domain experts. Results of expert evaluation may be the confirmation or denial of an extracted relation. One way to take this into account is to treat expert opinion as a final decision: if an expert denies a relation, it will be disabled or deleted. Multiple-expert aggregation can be used in this step to increase reliability.

Graph analysis algorithms can then be applied to discover a path among different drugs/substances/symptoms and how strong drugs-symptoms-substance connections are. This can help to answer questions such as "Can drug A cause symptom B?", "can drug A and drug B be administrated together?", and "can drug A be administrated after a dinner with food C?"

Such questions are entered by the end user, as described in more detail later. There may be a natural language based user interface. This user query will be parsed, translated into an internal format such as <drug>, <drug, symptom>, etc. for processing, and considered as the user query to be processed by the system. Users can be the general public or a specialist (pharmacist, researchers, or a drug safety authority), The results can present as 3-tuples as mentioned above, which can be paraphrased to give better readability.

Domain Extension

As discussed above, the same technology can be applied to extract information and construct domain knowledge graph of not only drug adverse reaction (drug and adverse symptoms) but also other types of interactions among different drugs, interaction between drugs and non-drugs substances, e.g. food, food supplements, and traditional therapies. This requires different ontologies, different dictionaries and potentially different data sources (or different data retrieval/crawling scripts).

Time Thresholds and User Queries

Figure 7:
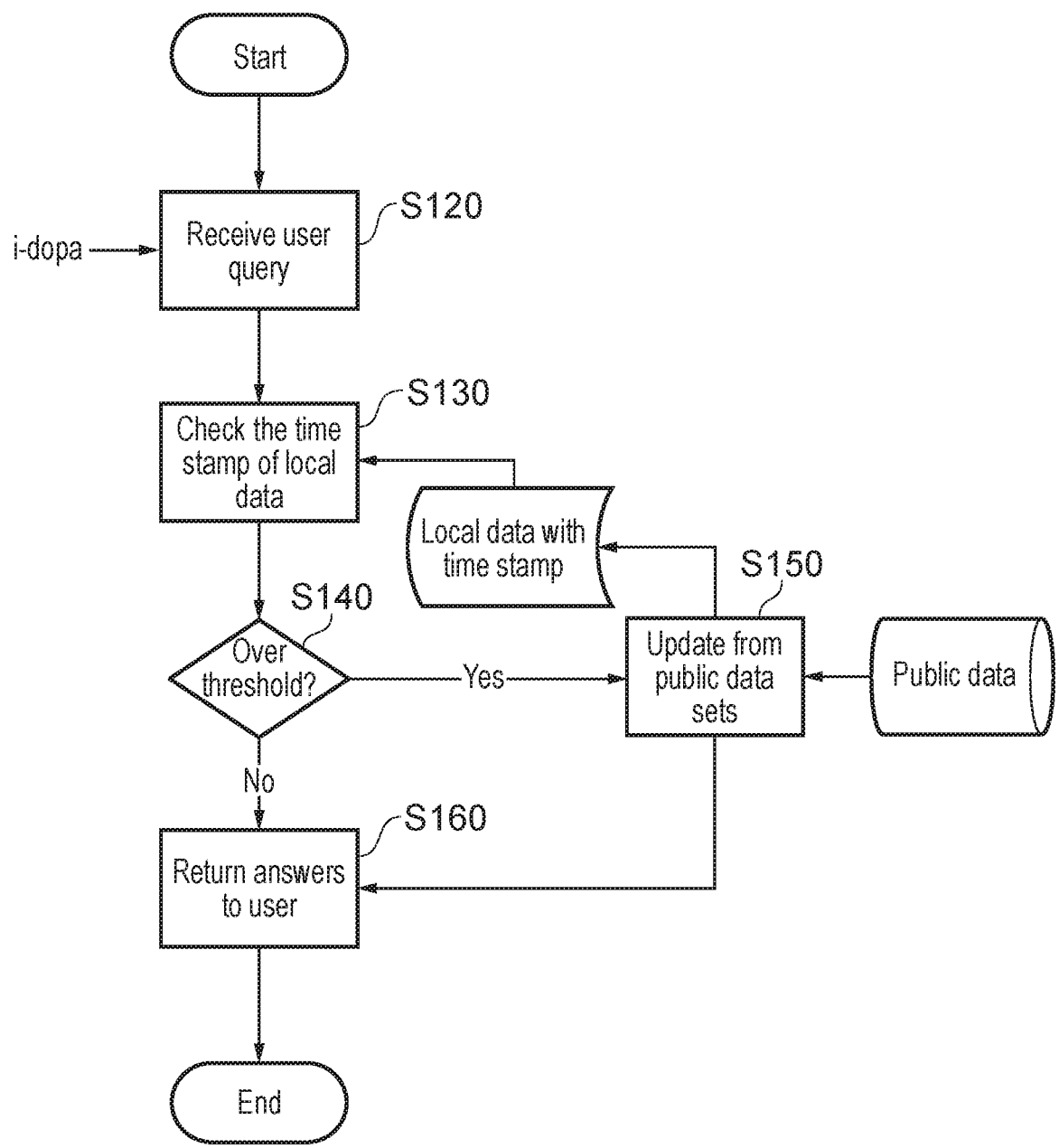
FIG. 7 is a flow chart of user input.

Once the relations have been created and quantified, they can be queried by the user. FIG. 7 is a flowchart of user input showing how user input as a query in step S120 can trigger a system update.

Local cached data are associated with a time stamp indicating when the data were last updated. If the time elapse is too long (over a threshold S140), at check S130 the public data monitoring module will update the local data, for example including a check whether the external data have been updated since the time stamp. If yes, live data extraction will be carried out in step S150, before returning an answer to the user in step S160.

Figure 8:
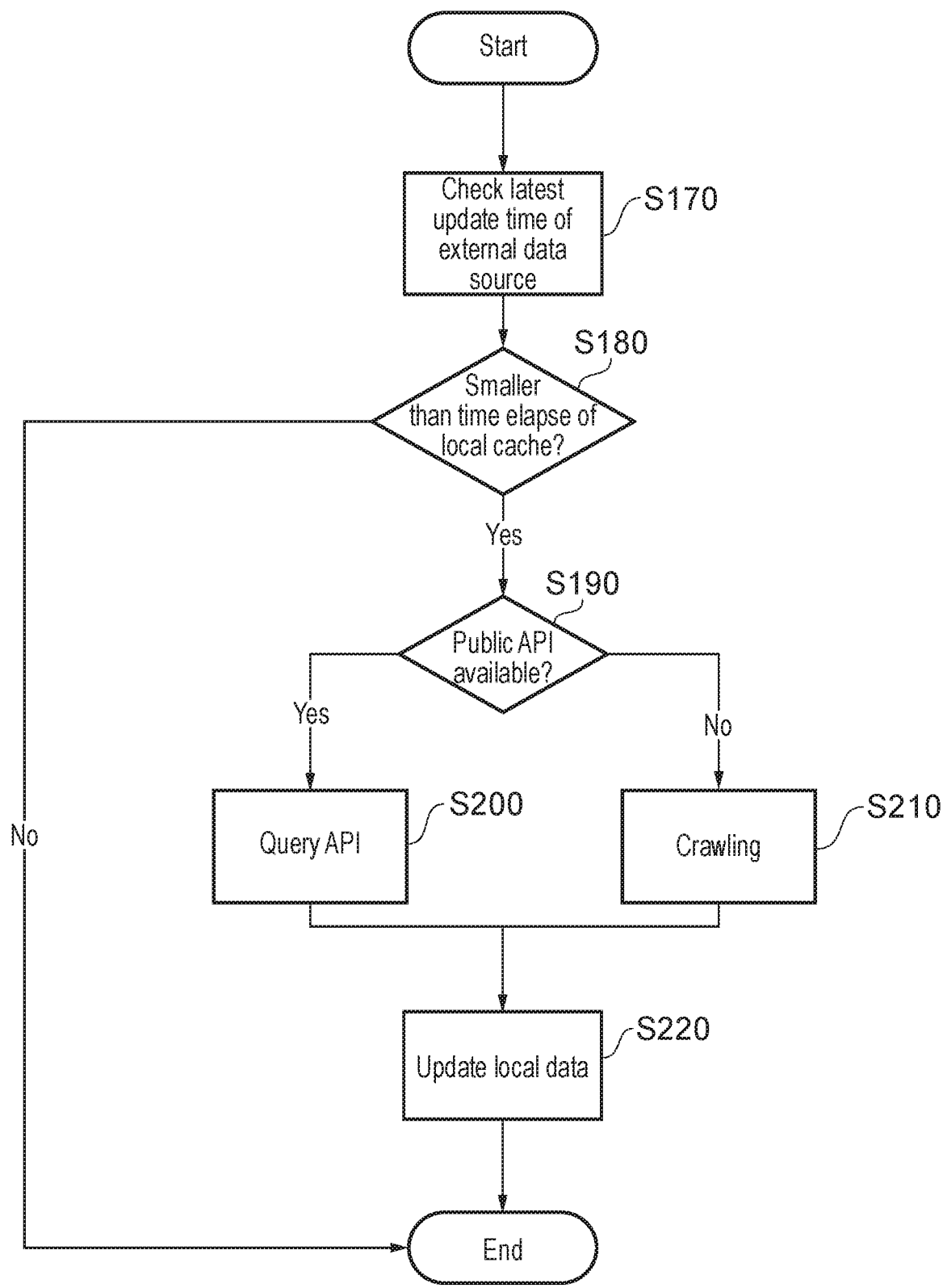
FIG. 8 is a flow chart of updating the stored information.

FIG. 8 shows an updating flowchart for the stored relations from each source. In step S170 the latest update time is retrieved. If the time elapsed is smaller than a threshold in S180, then the process ends for that data source. Otherwise there is a check S190 as to whether a public API (Application Programming Interface) is available. If so, the API is queried, S200. If not, crawling S210 takes place to retrieve the data. Local data is updated in step S220.

Returning to user queries, the order of which type of data (social media, publication, others) should be queried first can be customised by users. In practice, different types of data sources can be processed in parallel. There may be weights provided for social media, research and internet sources as mentioned above. Different individual data sources may also or alternatively have different quality measures (such as confidence value or weights, which can also be defined by users). By default, publications will be given higher priority than other source due to the publication's data quality. Social media will be given high value if users are seeking the most up-to-date, "in action" data.

An output of the system in internal format can be a 3-tuple (or triple)<drug, adr, confidence>, where drug is the drug name, adr presents a single adverse drug reaction detected in the data, and confidence may be a list of the following form for one or more sources [<data source, significance> . . . ]. Significance quantifies the drug-adr relation based on data source and knowledge extraction results.

For instance, <naproxen, ulcer, [<twitter, xxx>, <pubmed, xxx>, . . . ]> can be an exemplary output of queries regarding "naproxen".

This internal format can be paraphrased into natural language for better readability.

Scenarios:

The process is now split into several scenarios to illustrate use of the system.

Scenario 1: Off-Line Knowledge Extraction:

In this case, end users are not involved. Intervention from human experts is present for quality reasons.

Figure 9:
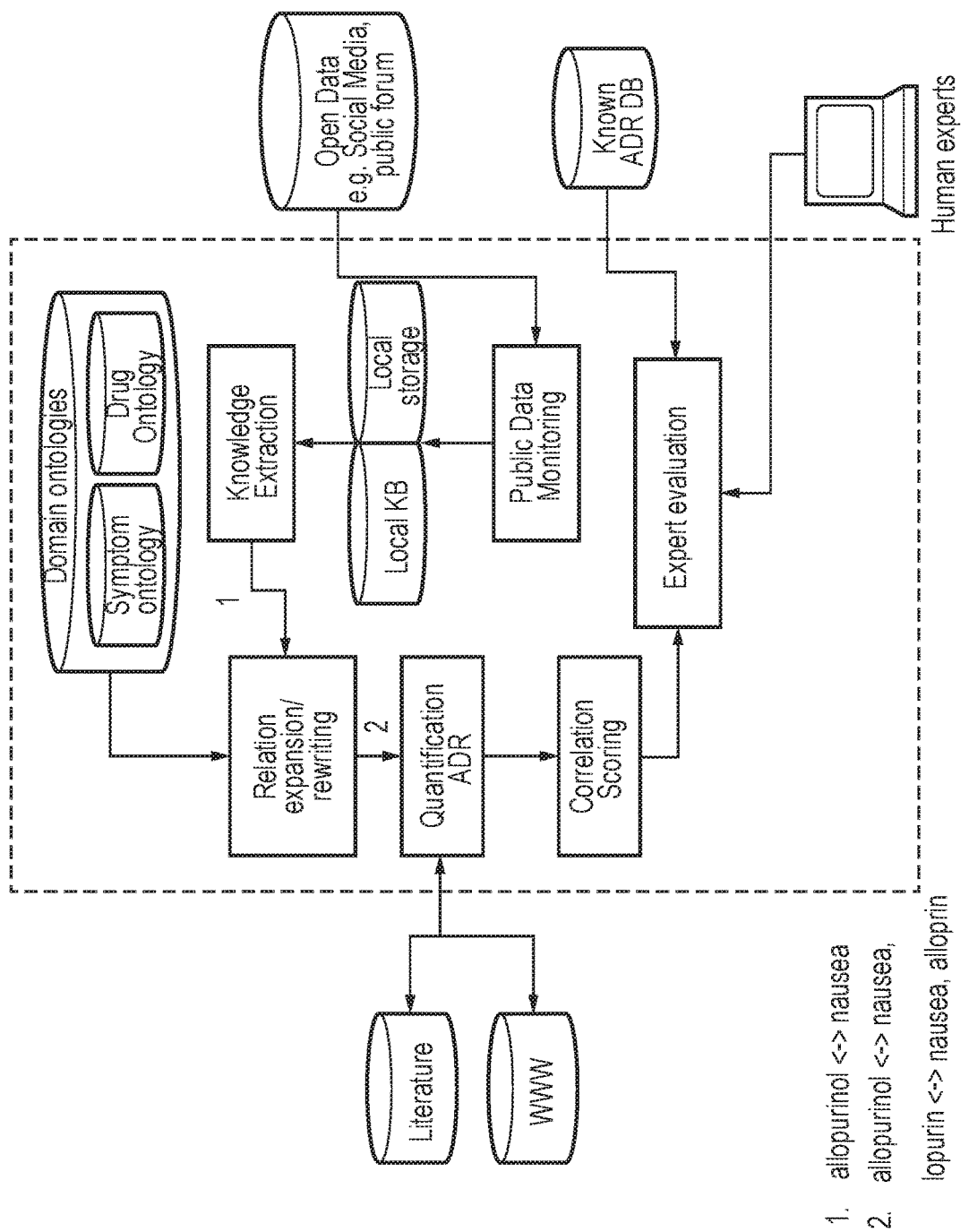
FIG. 9 is a block diagram of a system embodiment and a specific example of a learnt relation.

FIG. 9 is a modified form of FIG. 3 and the reader is referred to the description of FIG. 3 for like parts. The same applies to FIGS. 10 and 11. Here, only the "relation expansion" functionality of component 70 is represented because there is no user query. Also, two local storages are named: a local storage for caching data and a local Knowledge Base (KB) for final, confirmed relations.

In this scenario, the system periodically extracts knowledge from social media based on predefined scripts and verifies the extracted relations using multiple sources and methods. Interim and final results are stored in "local KB".

For instance, while monitoring social media, the initial relation can be extracted by the knowledge extraction module which then goes through the process as follows:

The relation found is <allopurinol, nausea, c>, with a real number as the initial social media based confidence.

Relation expansion takes place: <allopurinol, nausea>, <lopurin, nausea>, <allprin, nausea>, . . . all as potential candidates to be further quantified, so they can all inherit the social media score for the original relation. Otherwise, the score can be adjusted based on the hierarchical position, e.g. reducing it when moving up, and increasing when moving down. The relations are all then quantified using research/WWW.

Quantification ADR: all the candidate relations are subject to validation in this step based on literature and/or using GOOGLE search engine distance (for example). The results maybe: <allopurinol, nausea, c+b_i>, <allopurinol, nausea, c+b_j> where b_i and b_j can be either positive or negative and indicates the contribution to confidence level from a particular data source.

Correlation scoring aggregates all the extracted relations and computes a final score. The scoring can be a simple weighted average of all the scores or use more complicated algorithms.

Expert evaluation (optional) aggregates opinions from human experts, either adding such opinions as an offset on top of aggregated scores from a previous step or exercising a "True/False" veto power on the candidate list.

Scenario 2: Query Processing with Learnt Relations

Figure 10:
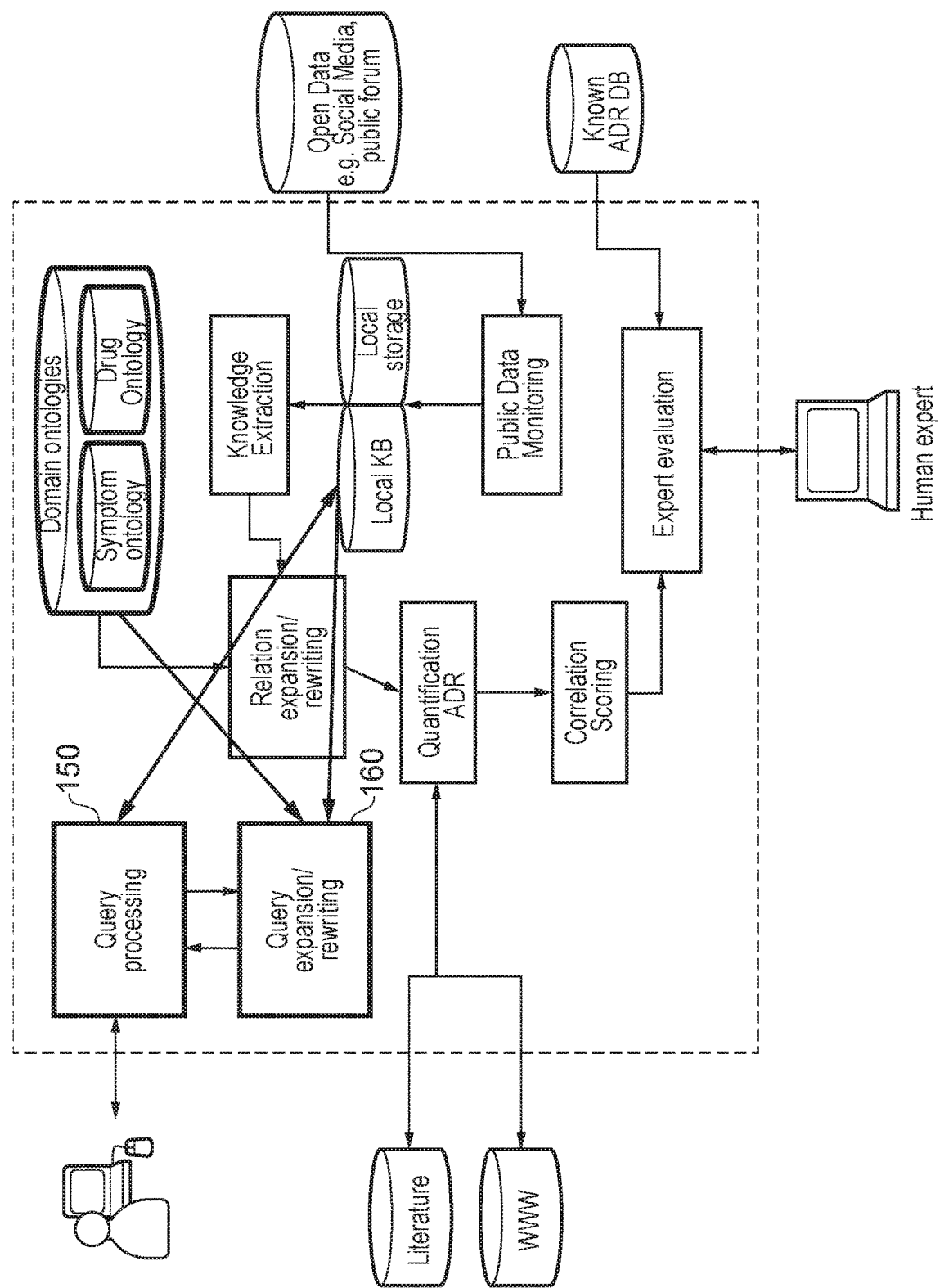
FIG. 10 is the block diagram of FIG. 9 including processing of a query.
Figure 11:
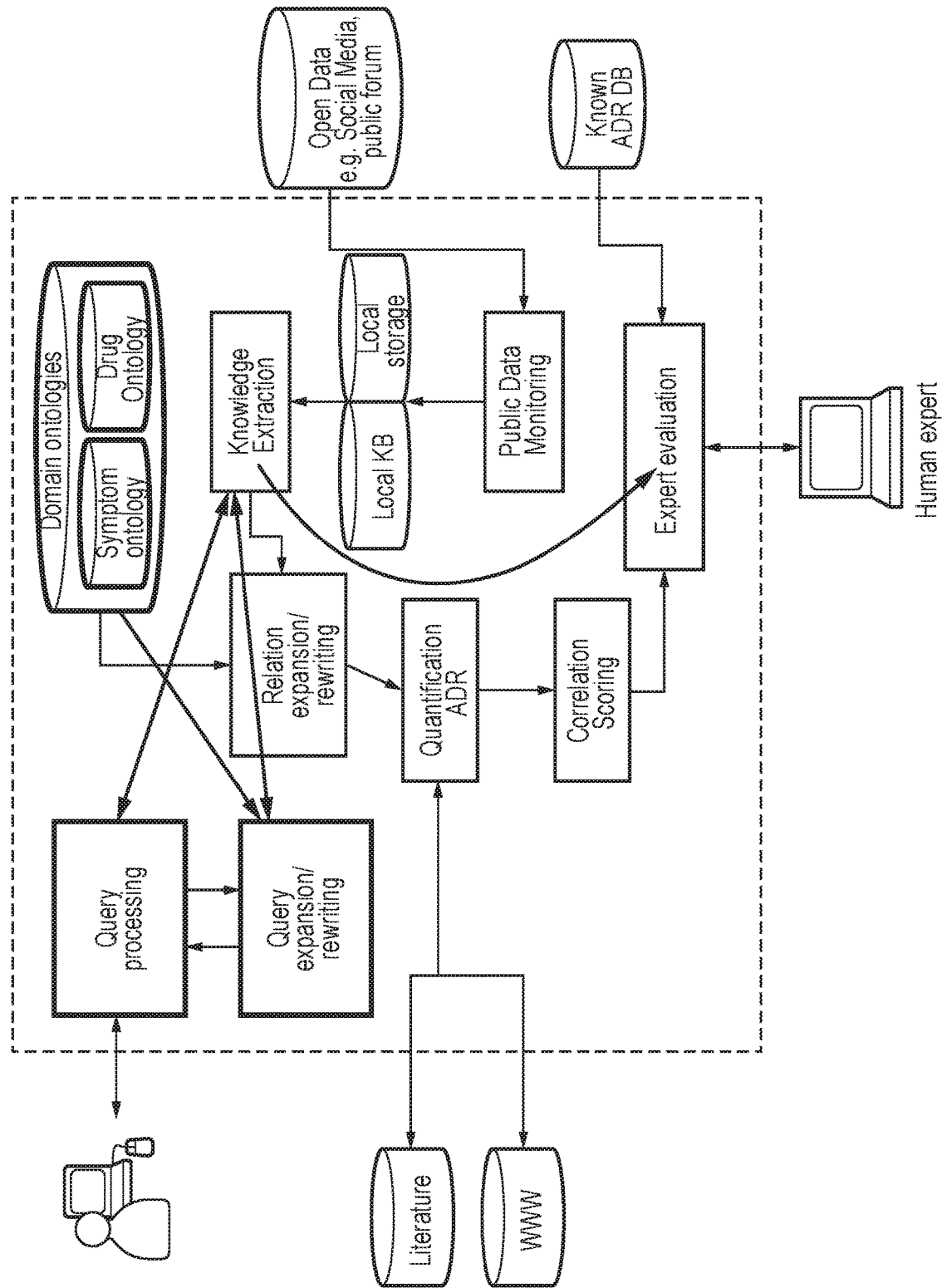
FIG. 11 is the block diagram of FIG. 9 including processing of a query when the queried relation was not stored in the system.

FIG. 10 is a modified form of FIG. 3, in which there is an extra module shown as query processing module 150, and a query expansion/re-writing module is shown as extra module 160. However module 160 could be part of module 70 as explained previously.

End users issue queries using key terms such as drug names. The system proceeds by:

Querying the local KB and retrieving learnt relations. If no matching queries are found then:

Expanding and rewriting initial queries to enlarge the query scope. This is based on domain ontologies as explained above for the relation expansion.

The process is carried out as follows:

Users submit queries in natural language regarding a particular drug, e.g. "all ADR of allopurinol" or "allopurinol causes headache".

This natural language based query is processed by query processing unit.

Internal query representation will be either used directly to query local KB or expanded using ontologies to gain better coverage.

Query expansion/rewriting can either broaden or narrow the original query and use the rewritten queries to retrieve answers from local KB.

Results are sent back to users by query processing unit.

Scenario 3: Online Learning

If the query cannot be satisfied (there is no relevant relation stored), an online extracting/learning process may be performed. In this case, the system may need to go through all the learning steps as outlined in the first scenario to find new relations.

On-line learning is a combination of the first two scenarios, when no results are found in a local KB. It may occur when the time elapsed between a local storage timestamp and external data sources' timestamp is over a predefined threshold (the external data source has updated since the last cache). In this case, data retrieval/crawling may be performed in real-time. The system then proceeds with all the learning/relation extraction steps to update the local KB. User interaction may be in such a way that 1) interim results are delivered to the end users along the process; and/or 2) users will be prompted when the process completes and new relations are ready to be used.

Figure 12:
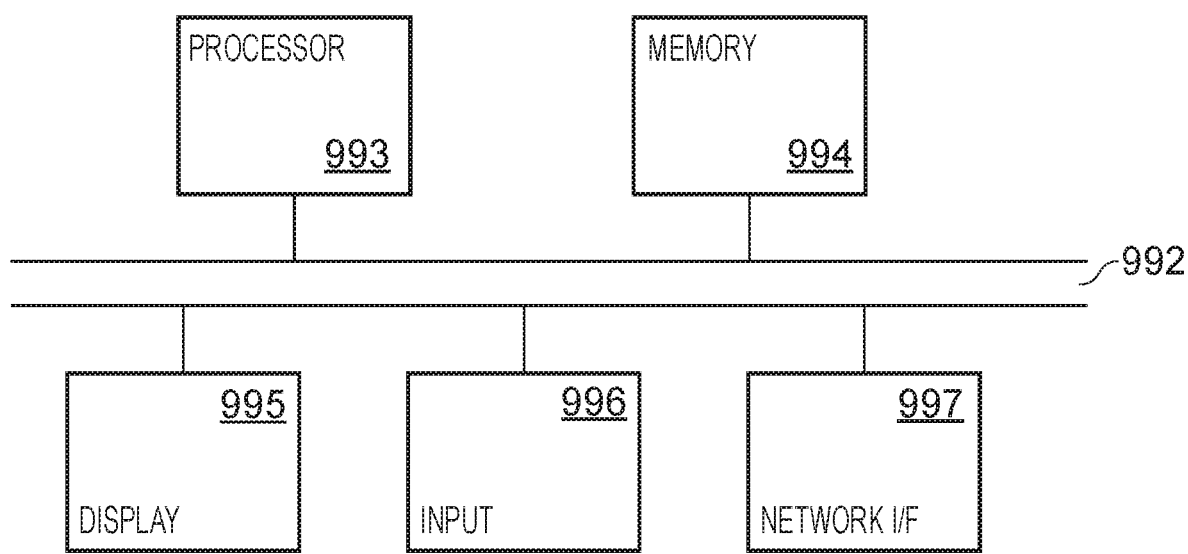
FIG. 12 is a block diagram of computer system hardware for use with invention embodiments.

FIG. 12 is a block diagram of a computing device, such as a server, which embodies the present invention, and which may be used to implement a method of producing and validating weighted relations between drugs and ADRs and a method of querying a graph of these relations. The computing device comprises a processor 993, and a memory 994. Optionally, the computing device also includes a network interface 997 for communication with other computing devices, for example with other computing devices of invention embodiments.

Figure 13:
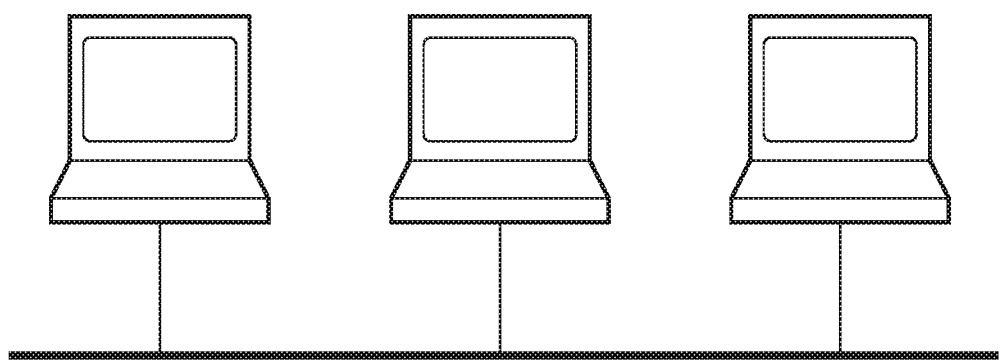
FIG. 13 is a block diagram of a computer network for use with invention embodiments.

For example, an embodiment may be composed of a network of such computing devices as shown in FIG. 13. Optionally, the computing device also includes one or more input mechanisms such as keyboard and mouse 996, and a display unit such as one or more monitors 995. These can be provided for the input of user queries to query processing module 150 and the output of results to the user. The same or a different interface can be provided for expert input. The components are connectable to one another via a bus 992.

The memory 994 may include a computer readable medium, which term may refer to a single medium or multiple media (e.g., a centralized or distributed database and/or associated caches and servers) configured to carry computer-executable instructions or have data structures stored thereon. Computer-executable instructions may include, for example, instructions and data accessible by and causing a general purpose computer, special purpose computer, or special purpose processing device (e.g., one or more processors) to perform one or more functions or operations. Thus, the term "computer-readable storage medium" may also include any medium that is capable of storing, encoding or carrying a set of instructions for execution by the machine and that cause the machine to perform any one or more of the methods of the present disclosure. The term "computer-readable storage medium" may accordingly be taken to include, but not be limited to, solid-state memories, optical media and magnetic media. By way of example, and not limitation, such computer-readable media may include non-transitory computer-readable storage media, including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices).

The processor 993 is configured to control the computing device and execute processing operations, for example executing code stored in the memory to implement the various different functions of the modules, including the public data monitoring module 30, knowledge extraction module 40, relation refinement module 70 and quantification ADR module 80 described in detail herein. The memory 994 stores data being read and written by the processor 993. For example, the public data monitoring module 30 may comprise processing instructions stored on a portion of the memory 994, the processor 993 to execute the processing instructions, and a portion of the memory 994 acting as the local KB stores relations during the execution of the processing instructions.

As referred to herein, a processor may include one or more general-purpose processing devices such as a microprocessor, central processing unit, or the like. The processor may include a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also include one or more special-purpose processing devices such as an application specific integrated circuit (ASIC), a field programmable gate array (FPGA), a digital signal processor (DSP), network processor, or the like. In one or more embodiments, a processor is configured to execute instructions for performing the operations and steps discussed herein.

The display unit 995 may display a representation of data stored by the computing device (such as a graph of the relations or individual relations in the form of triples) and may also display a cursor and dialog boxes and screens enabling interaction between a user and/or expert and the programs and data stored on the computing device. The input mechanisms 996 may enable a user to input queries, data and instructions to the computing device.

The network interface (network I/F) 997 may be connected to a network, such as the Internet, and is connectable to other such computing devices via the network. The network I/F 997 may control data input/output from/to other apparatus via the network. Other peripheral devices such as microphone, speakers, printer, power supply unit, fan, case, scanner, trackerball etc. may be included in the computing device.

Accordingly, methods embodying the present invention may be carried out on a computing device such as that illustrated in FIG. 12. For instance, modules as illustrated in FIG. 1 and described above may be implemented as software code stored in the memory 994 and executed by the processor 993. Such a computing device need not have every component illustrated in FIG. 12, and may be composed of a subset of those components. A method embodying the present invention may be carried out by a single computing device in communication with one or more data storage servers via a network. The computing device may be a data storage itself storing the relations/a graph of the relations.

A method embodying the present invention may be carried out by a plurality of computing devices operating in cooperation with one another. One or more of the plurality of computing devices may be a data storage server storing at least a portion of the relations/a graph of the relations.

Hence the system can run on either one computer or have part of its functionalities distributed to multiple computers for better performance. For instance the social media monitoring can be implemented by geographically distributed computer clusters that reside close to the data sources. The results can then be transported to computers responsible for the next step, over a computer network.

Benefits

Embodiments of the invention can offer any of the following:

1. A method to detect and extract ADRs that may not be formally documented in drug manual or may not be discovered during clinical trials.
2. A method to quantify the discovered ADRs using trusted sources of information.
3. A method to quantify the discovered ADRs using the entire Internet as data repository.
4. A semantic-based mechanism to enrich the discovery process.
5. An automatic score scheme that helps to decide whether a discovered ADR is worth further investigation. The discovered (d, s) is from social media which provides the most up-to-date data. The system further evaluates such discovered "knowledge" with those from more trust-worthy sources. This evaluation is done automatically, presenting a final score for users to consume.
6. A pharmacovigilance mechanism that monitors the latest information (latest trends) to discover ADRs and ensure safety of medicines.

This can work as a complementary measure to documented ADRs from medical research and from clinical trials performed by pharmaceutical companies. The discovery of a relation may trigger an alarm to the user if it falls under certain criteria, for example associated with the severity of the ADR in the relation, perhaps coupled with the level of confidence.

Although a few embodiments have been shown and described, it would be appreciated by those skilled in the art that changes may be made in these embodiments without departing from the principles and spirit of the invention, the scope of which is defined in the claims and their equivalents.

The invention claimed is:

1. An apparatus to produce and validate weighted social media relations between drugs and adverse drug reactions (ADRs), the system comprising:
    a processor; and
    a memory to store instructions, which when executed by the processor cause the processor to perform a process to:
        monitor information of a social media system for links between drugs and the ADRs;
        extract a social media relation, among social media relations, between a drug among the drugs and an ADR among the ADRs using named entity recognition and to provide a weighted social media relation between the drug and the ADR which is weighted based on a confidence level of a link among the links between the drug and the ADR in the social media system;
        store the extracted social media relation between the drug and the ADR in association with the weighted social media relation;
        use domain knowledge in an ontology database to apply a refinement process to the named entity recognition for the drug and the ADR, respectively, to refine the weighted social media relation in accordance with one or more ontologies of drug names and/or of ADRs;
        quantify the confidence level of the refined weighted social media relation based upon:
            drugs and ADR links extracted from research publications and/or from clinical trial reports to quantify a research weight to be included in the refined weighted social media relation, based on a ratio of evidence linking the drug and the ADR to overall mentions of the drug in the research publications and/or the clinical trial reports, and
            search results of an Internet search engine from a search of the World Wide Web over the Internet for the drug and the ADR, to obtain a number of search hits returned to quantify an internet weight to be included in the refined weighted social media relation based on the search results; and
        compute the quantified confidence level of the refined weighted social media relation based upon information resulting from a user-defined strategy to give a weighting to each of the social media weight, the research weight and the internet weight, and aggregating the social media weight, the research weight and the internet weight to provide information indicating a validation of the quantified confidence level of the refined weighted social media relation.

2. The apparatus according to claim 1, wherein the weighted social media relation between the drug and the ADR is in form of a triple data set of <drug, ADR, c> where c is the confidence level corresponding to a weight.

3. The apparatus according to claim 1, wherein to refine the weighted social media relation includes expansion of the weighted social media relation to include equivalent drug names and equivalent ADRs and/or refinement of the weighted social media relation to replace the ADR with a more or less specific ADR.

4. The apparatus according to claim 1, wherein the confidence level of the weighted social media relation is above a threshold confidence level.

5. The apparatus according to claim 1, wherein the internet weight is based on a search engine distance between the drug and the ADR.

6. The apparatus according to claim 1, wherein the process is to,
monitor the social media system for other links between the drugs and other substances;
extract a drug-substance relation between a drug among the drugs and a substance among the other substances using named entity recognition and to provide a weighted social media drug-substance relation between the drug and the substance which is based on a confidence level of a link among the links between the drug and the substance in the social media system;
store the extracted drug-substance relation between the drug and the substance in association with the weighted social media drug-substance relation;
use the ontology database to refine the weighted social media drug-substance relation in accordance with one or more ontologies of drug names and/or of substances; and
quantify the confidence level of the refined weighted social media drug-substance relation based upon,
substance and drug data extracted from research publications and/or from clinical trial reports to quantify a research weight for the weighted social media drug-substance relation, and/or
search results of an internet search engine searching the World Wide Web over the Internet for the drug and the ADR, to obtain a number of search hits returned quantifying an internet weight for the weighted social media drug-substance relation based on the searching.

7. A system to allow a user to assess relations between drugs and adverse drug reactions (ADRs), the system comprising:
an apparatus including a processor and a memory storing instructions, which when executed by the processor cause the processor to perform a process to produce and validate weighted social media relations between the drugs and the ADRs in a knowledge base according to claim 1; and
a user interface allowing input of a user query for a social media relation between the drug and the ADR,
wherein the processor is to,
rewrite the query using a domain ontology; and
retrieve an answer to the rewritten query from the knowledge base.

8. The system according to claim 7, wherein if no relation is found in the knowledge base, the processor is to further monitor the information from the social media system in real time.

9. A method of producing and validating weighted social media relations between drugs and adverse drug reactions (ADRs), the method comprising:
by at least one processor,
monitoring information of a social media system for links between drugs and the ADRs;
extracting a social media relation, among social media relations, between a drug among the drugs and an ADR among the ADRs using named entity recognition and to provide a weighted social media relation between the drug and the ADR which is weighted based on a confidence level of a link among the links between the drug and the ADR in the social media system;
storing the extracted social media relation between the drug and the ADR in association with the weighted social media relation;
using domain knowledge in an ontology database to apply a refinement process to the named entity recognition for the drug and the ADR, respectively, to refine the weighted social media relation in accordance with one or more ontologies of drug names and/or of ADRs;
quantifying the confidence level of the refined weighted social media relation based upon:
drugs and ADR links extracted from research publications and/or from clinical trial reports to quantify a research weight to be included in the refined weighted social media relation, based on a ratio of evidence linking the drug and the ADR to overall mentions of the drug in the research publications and/or the clinical trial reports, and
search results of an Internet search engine from a search of the World Wide Web over the Internet for the drug and the ADR, to obtain a number of search hits returned to quantify an internet weight to be included in the refined weighted social media relation based on the search results; and
providing information indicating a validation of the quantified confidence level of the refined weighted social media relation resulting from a computation of the quantified confidence level of the refined weighted social media relation based upon information resulting from a user-defined strategy to give a weighting to each of the social media weight, the research weight and the internet weight, and aggregating the social media weight, the research weight and the internet weight.

10. A method of allowing a user to query for a link between a drug and an adverse drug reaction (ADR), the method comprising:
by at least one processor,
allowing input of a user query for a social media relation between the drug and the ADR stored in a knowledge base according to claim 9;
rewriting the query using a domain ontology; and
retrieving a query answer for the rewritten query from the knowledge base.

* * * * *